US009815756B2

(12) United States Patent
Schmidt et al.

(10) Patent No.: US 9,815,756 B2
(45) Date of Patent: Nov. 14, 2017

(54) METHODS AND APPARATUSES FOR PHENOL FRACTIONATION IN A SINGLE DIVIDING WALL COLUMN

(71) Applicant: UOP LLC, Des Plaines, IL (US)

(72) Inventors: Robert J. Schmidt, Barrington, IL (US); Charlotte Y. Fang, Houston, TX (US); Russell C. Schulz, Glen Ellyn, IL (US); Xin X. Zhu, Long Grove, IL (US); Scott R. Keenan, Marlton, NJ (US); Chad A. Williams, Arlington Heights, IL (US); Heather D. Tsihlis, Buffalo Grove, IL (US); Jose L. Miramontes, Madrid (ES); Robert E. Tsai, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/469,251

(22) Filed: Mar. 24, 2017

(65) Prior Publication Data

US 2017/0283350 A1 Oct. 5, 2017

Related U.S. Application Data

(60) Provisional application No. 62/316,425, filed on Mar. 31, 2016.

(51) Int. Cl.
*C07C 45/82* (2006.01)
*C07C 37/74* (2006.01)
*C07C 45/90* (2006.01)

(52) U.S. Cl.
CPC .............. *C07C 37/74* (2013.01); *C07C 45/90* (2013.01)

(58) Field of Classification Search
CPC .................................. C07C 45/82; C07C 37/74
USPC .......................................................... 568/411
See application file for complete search history.

(56) References Cited

U.S. PATENT DOCUMENTS

| 5,905,178 A * | 5/1999 | Hildreth ................. C07C 7/163 |
| | | 203/DIG. 6 |
| 6,169,215 B1 * | 1/2001 | Levin ..................... B01J 23/002 |
| | | 568/385 |
| 7,141,700 B1 * | 11/2006 | Schmidt .................. C07C 1/20 |
| | | 568/385 |
| 7,417,003 B2 * | 8/2008 | Schmidt ............... B01J 29/7007 |
| | | 502/63 |
| 2010/0108487 A1 * | 5/2010 | Townsend .............. B01D 3/007 |
| | | 203/26 |
| 2013/0068609 A1 * | 3/2013 | Bhargava ............... B01D 3/141 |
| | | 203/87 |

* cited by examiner

*Primary Examiner* — Sikarl Witherspoon

(57) ABSTRACT

This present disclosure relates to processes and apparatuses for use of a single dividing wall distillation column for phenol fractionation. More specifically, the present disclosure relates to processes and apparatuses for phenol fractionation by combining crude acetone column and cumene-AMS column into a single dividing wall distillation column. The proper allocation of steam or water injection, chemical treatment reactor and internal liquid phase separator, the positioning of the side draw enables high yield of acetone and phenol.

20 Claims, 3 Drawing Sheets

METHODS AND APPARATUSES FOR PHENOL FRACTIONATION IN A SINGLE DIVIDING WALL COLUMN

CROSS-REFERENCE TO RELATED APPLICATION

This application claims priority from Provisional Application No. 62/316,425 filed Mar. 31, 2016, the contents of which are hereby incorporated by reference.

FIELD

This present disclosure relates to processes apparatuses for work-up by distillation of cleavage product mixtures produced in the cleavage of alkylaryl hydroperoxides. More specifically, the present disclosure relates to processes and apparatuses for use of a single dividing wall column to combine all the functions of crude acetone column and cumene-alphamethylstyrene (AMS) column.

BACKGROUND

Phenol is manufactured via air oxidation of cumene to cumene hydroperoxide (CHP), followed by acid-catalyzed cleavage of the latter to phenol and acetone, and known as CHP decomposition. CHP decomposition is a very exothermic reaction which is normally carried out on a commercial scale in continuous stirred or back-mixed reactors. In such reactors only a small fraction of CHP is unreacted at any given time and the reaction medium consists essentially of the products of decomposition of CHP, i.e., phenol and acetone, plus any solvent (e.g., cumene) and other materials added with CHP to the reactor. During cumene oxidation small amounts of dimethyl phenyl carbinol (DMPC) and acetophenone are also formed. In the presence of acid catalyst, DMPC dehydrates to alphamethylstyrene (AMS), a useful by-product.

The traditional design of phenol fractionation flow scheme includes two columns that are used to separate the acetone, cumene, and AMS in the fractionation feed from the phenol. Acetone and a portion of the cumene and water are first distilled to the overheads of the crude acetone column (first column), which operates at slightly above the atmospheric pressure. Acids in the overhead streams would lead to fouling in the subsequent system. The bottoms, containing the remainder of the cumene and water and the bulk of formic acid and acetic acid, along with essentially all of the AMS, phenol and higher-boiling by-products are routed to the cumene-AMS column (second column), which operates at fairly deep vacuum. However, there is need to separate the phenol contaminants and impurities in a separate system downstream the phenol fractionation column with two columns.

The use of such multiple systems for phenol fractionation results in increased capital equipment costs and operating costs. The conventional design of single distillation column known in the prior art do not yield high recoveries of acetone and phenol. There is a need for a new process and apparatus to efficiently operate the phenol unit with significant reduction in the capital and operating costs. Also, there is a need for an improved and more economical process and simplified apparatus design for the phenol fractionation that can improve the yield of phenol and acetone.

SUMMARY

An embodiment of the subject matter is a process for the work-up by distillation of cleavage product mixtures produced in the cleavage of alkylaryl hydroperoxides, which comprises resolving the cleavage product mixture into at least three fractions in a single distillation step by feeding the cleavage product mixture to a side of a dividing wall distillation column. A first fraction comprising ketone is removed at the top of the dividing wall distillation column comprises at least 95% of a ketone present in the cleavage product before the distillation step. A second fraction comprising substituted or unsubstituted phenol is removed at the bottom of the dividing wall distillation column. A third fraction comprising unreacted mono-, di- and/or trialkyl substituted benzene, water, and hydroxy ketone is removed as side stream, whereby the side stream take-off is situated below the feed of cleavage product mixture to the dividing wall distillation column.

Another embodiment of the subject matter is a process for the work-up by distillation of cleavage product mixtures produced in the cleavage of alkylaryl hydroperoxides, which comprises resolving the cleavage product mixture into at least three fractions in a single distillation step by feeding the cleavage product mixture to a side of a dividing wall distillation column. A first fraction comprising ketone is removed at the top of the dividing wall distillation column comprises at least 95% of a ketone present in the cleavage product before the distillation step. A second fraction comprising substituted or unsubstituted phenol is removed at the bottom of the dividing wall distillation column. A third fraction comprising unreacted mono-, di- and/or trialkyl substituted benzene, water and hydroxy ketone is removed as side stream of the dividing wall distillation column, whereby the side stream take-off is situated below the feed of cleavage product mixture to the dividing wall distillation column. The third fraction is sent to a chemical treatment reactor.

A further embodiment of the subject matter is a process for the work-up by distillation of cleavage product mixtures produced in the cleavage of alkylaryl hydroperoxides, which comprises resolving the cleavage product mixture into at least three fractions in a single distillation step by feeding the cleavage product mixture to a side of a dividing wall distillation column. A first fraction comprising ketone is removed at the top of the dividing wall distillation column comprises at least 95% of a ketone present in the cleavage product before the distillation step. A second fraction comprising substituted or unsubstituted phenol is removed at the bottom of the dividing wall distillation column. The second fraction is sent to a chemical treatment reactor. A third fraction comprising unreacted mono-, di- and/or trialkyl substituted benzene, water and hydroxy ketone is removed as side stream of the dividing wall distillation column, whereby the side stream take-off is situated below the feed of cleavage product mixture to the dividing wall distillation column. The third fraction overflows a liquid collection apparatus and flows into a decanter.

It is an advantage of the subject matter to combine all the functions of the crude acetone column and cumene-AMS column while maintaining the same phenol and acetone quality and also avoid fouling, undesirable reactions and corrosions. A dividing wall distillation column may be used to replace two distillation column in series. However, there are several challenges associated with the use of dividing wall column with respect to the relative volatility of the boiling components, intermediate distillate stream flow rate and operating conditions. The present subject matter seeks to provide a novel process and apparatus with reduced capital and operating costs and provides solution to the challenges in implementing a dividing wall column by proper allocation of steam/water injection, decanter and a chemical treatment reactor. A benefit of the subject matter is that the combination of control system and column and tray design enables stable, robust and economical operation of dividing wall column and enhanced acetol distillation.

Additional objects, advantages and novel features of the examples will be set forth in part in the description which follows, and in part will become apparent to those skilled in the art upon examination of the following description or may be learned by production or operation of the examples. The objects and advantages of the concepts may be realized and attained by means of the methodologies, instrumentalities and combinations particularly pointed out in the appended claims.

DETAILED DESCRIPTION

The following description is not to be taken in a limiting sense, but is made merely for the purpose of describing the general principles of exemplary aspects. The scope of the present disclosure should be determined with reference to the claims.

Figure 1:
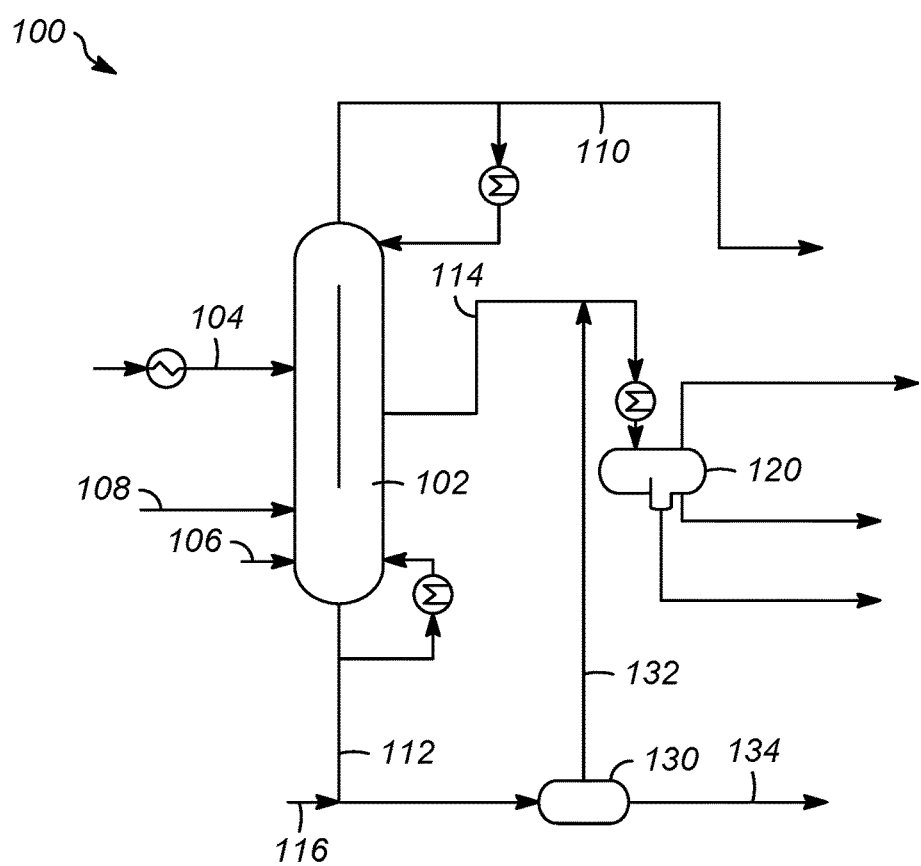
FIG. 1 is a flow scheme for the process of the present subject matter.

A general understanding of the process for the work-up by distillation of cleavage product mixtures produced in the cleavage of alkylaryl hydroperoxides, to resolve the cleavage product mixture into at least three fractions in a single distillation using a dividing wall distillation column can be obtained by reference to FIG. 1. FIG. 1 has been simplified by the deletion of a large number of apparatuses customarily employed in a process of this nature, such as vessel internals, temperature and pressure controls systems, flow control valves, recycle pumps, etc. which are not specifically required to illustrate the performance of the subject matter. Furthermore, the illustration of the process of this subject matter in the embodiment of a specific drawing is not intended to limit the subject matter to specific embodiments set out herein.

The present subject matter, as shown in FIG. 1, includes a distillation column and a reactor system 100 to separate the cleavage product mixture into at least three fractions in a single dividing wall distillation column 102 of the reactor system. Many configurations of the present invention are possible, but specific embodiments are presented herein by way of example. A feed of a cleavage product mixture produced in the cleavage of alkylaryl hydroperoxides is passed to the dividing wall distillation column 102 in line 104. Steam is passed along the feed mixture to the dividing wall distillation column 102 in line 106 for stripping. Steam or water is injected between the bottom of the dividing wall distillation column 102 and an injection point in the bottom-third of the dividing wall distillation column 102. The feed rate may be about 75,757 kg/h and the feed rate of the components of the cleavage product mixture comprising acetone, phenol, cumene and alpha-methyl styrene (AMS) may be about 23,570 kg/h, 38,768 kg/h, 9,824 kg/h and 1,614 kg/h respectively. The cleavage product mixture before the work-up distillation comprises a concentration of about 40 mol % ketone, about 40 mol % substituted or unsubstituted phenol, and remainder comprises of unreacted mono-, di- and/or trialkyl substituted benzene and hydroxy ketone.

A first fraction comprising ketone is taken at top of the dividing wall distillation column 102 in line 110. The ketone fraction taken at the top of the dividing wall distillation column 102 may be acetone. The product rate of the first fraction taken at the top of the dividing wall distillation column 102 may be about 30,353 kg/h. The product rate of the acetone in the first fraction taken at the top of the dividing wall distillation column 102 may be about 23,555 kg/h. There may be at least about 95% of ketone present in the cleavage product before the distillation step. The use of a dividing wall column for distillation enables better separation of acetone. The first fraction removed from the dividing wall distillation column 102 comprises more than about 99.9% of acetone recovered in line 110. There may be relatively small amounts of cumene and water along with the acetone in the first fraction taken at the overhead of the dividing wall distillation column 102.

A second fraction comprising substituted or unsubstituted phenol is taken at the bottom of the dividing wall distillation column 102 in line 112. The product rate of the second fraction taken at the bottom of the dividing wall distillation column 102 may be about 43,658 kg/h. The product rate of the phenol in the second fraction taken at the bottom of the dividing wall distillation column 102 may be about 42,708 kg/h. The second fraction removed from the dividing wall distillation column 102 comprises more than about 98% of phenol recovered in line 112. The heavy hydrocarbons, acetol or hydroxyacetone are removed along with phenol in the second fraction at the bottom of the dividing wall distillation column 102. The concentration of acetol in the second fraction of the dividing wall distillation column 102 may be about 100 wt-ppm to about 500 wt-ppm.

A third fraction comprising unreacted mono-, di- and/or trialkyl substituted benzene, water, and hydroxy ketone are taken as side stream of the dividing wall distillation column 102 in line 114. The side stream taken-off in line 114 may be situated below the feed of cleavage product mixture to the dividing wall distillation column 102. The liquid rate of the side draw in the third fraction taken as the side stream the dividing wall distillation column 102 may be about 8,603 kg/h. The waste water rate in the third fraction taken as the side stream of the dividing wall distillation column 102 may be 835 kg/h. The remainder of cumene, water, organic acids and essentially all of the alpha-methyl styrene (AMS) are removed as side stream of the dividing wall distillation column 102 in line 114. The steam injection point enables most of the formic acid and acetic acid to distill to the cumene-alpha-methyl styrene (AMS) side draw so that the acid content is within the limits for downstream acetone purification. The recovery of acetol into the side stream of the dividing wall distillation column may be about 50% relative to the feed. The mixture comprising cumene and alpha-methyl styrene (AMS) in the third fraction may be sent to a phenol recovery unit 120. The side draw of the dividing wall distillation column 102 may be a two-phase mixture comprising water and organic phase. The side draw in line 114 may be cooled to separate the two-phase mixture before sending the stream to a phenol recovery unit 120.

The second fraction removed at the bottom of the dividing wall distillation column 102 in line 112 is passed to a chemical treatment reactor 130. The chemical treatment reactor 130 may be located with the dividing wall distillation column 102. The chemical treatment reactor 130 may be located outside the dividing wall distillation column 102.

Amine is passed along with the second fraction to the chemical treatment reactor 130 in line 116. Acetol and other carbonyl impurities are removed from the second fraction of the dividing wall distillation column 102 by treating the second fraction with amine in the chemical treatment reactor 130. Alternatively, the byproduct comprising water may be removed by recycling the material in line 132 from the chemical treatment reactor 130 to the bottoms of bottom of the dividing wall distillation column 102. The streams in lines 114 and 132 comprising cumene, alpha-methyl styrene (AMS), water may be passed to the phenol recovery unit 120 for further recovery. Phenol free of acetol and other impurities is removed in line 134 from the chemical treatment reactor 130. The phenol removed from the chemical treatment reactor 130 may be passed to a crude phenol column. Phenol may be recycled to the dividing wall distillation column 102 in line 108. The phenol recycle rate may be 4,656 kg/h.

The operating conditions for the dividing wall distillation column 102 will include an operating temperature in the range of from about 174° C. to about 225° C. and a pressure in the range of about 70 kPa to about 345 kPa. The tray spacing of the dividing wall distillation column 102 below the feed of cleavage product mixture is increased from about 680 mm to about 1450 mm. The tray spacing of the dividing wall distillation column 102 above the side stream is increased from about 450 mm to about 2100 mm.

Figure 2:
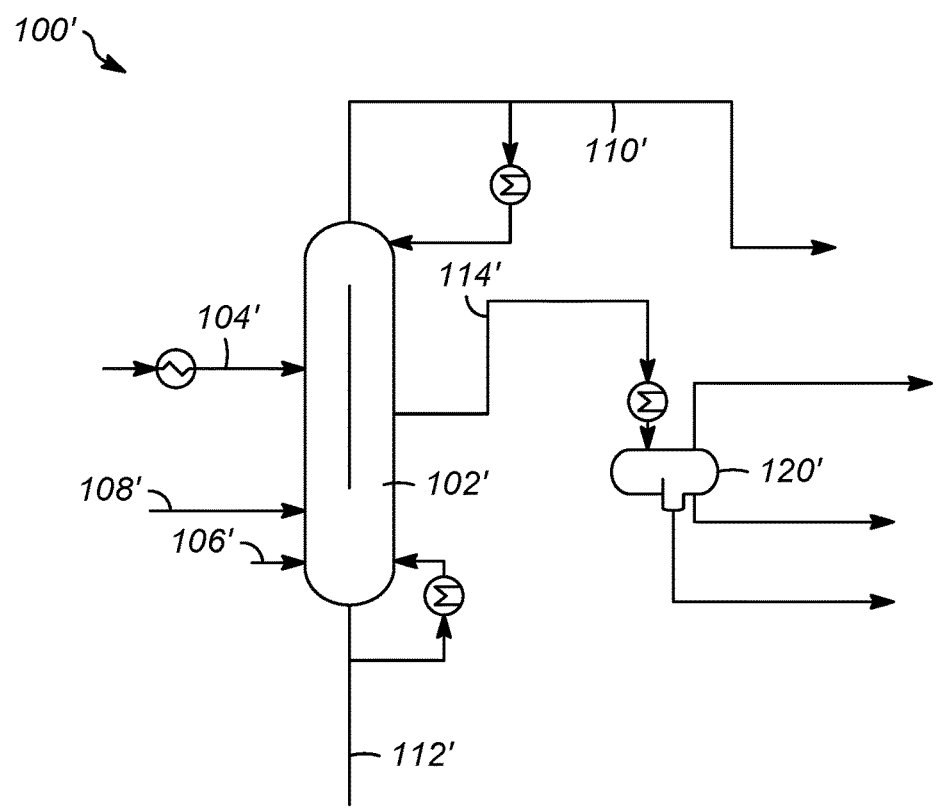
FIG. 2 is alternative embodiment of the process of the present subject matter shown in FIG. 1.

Turning now to FIG. 2, alternative embodiment of the process of the present subject matter shown in FIG. 1 to separate the cleavage product mixture into at least three fractions in a single dividing wall distillation column. The embodiment of FIG. 2 differs from the embodiment of FIG. 1 in non-inclusion of the chemical treatment reactor. The similar components in FIG. 2 that were described above for FIG. 1 will not be described again for FIG. 2. Many of the elements in FIG. 2 have the same configuration as in FIG. 1 and bear the same reference number. Elements in FIG. 2 that correspond to elements in FIG. 1 but have a different configuration bear the same reference numeral as in FIG. 1 but are marked with a prime symbol (').

The present subject matter, as shown in FIG. 2, includes distillation column and a reactor system 100' to separate the cleavage product mixture into at least three fractions in a single dividing wall distillation column 102' of the reactor system. Many configurations of the present invention are possible, but specific embodiments are presented herein by way of example. A feed of a cleavage product mixture produced in the cleavage of alkylaryl hydroperoxides is passed to the dividing wall distillation column 102' in line 104'. Steam is passed along the feed mixture to the dividing wall distillation column 102' in line 106' for stripping. Steam or water is injected between the bottom of the dividing wall distillation column 102' and an injection point in the bottom-third of the dividing wall distillation column 102'. The feed rate may be about 75,757 kg/h and the feed rate of the components of the cleavage product mixture comprising acetone, phenol, cumene and alpha-methyl styrene (AMS) may be about 23,570 kg/h, 38,768 kg/h, 9,824 kg/h and 1,614 kg/h respectively. The cleavage product mixture before the work-up distillation comprises a concentration of about 40 mol % ketone, about 40 mol % substituted or unsubstituted phenol, and remainder comprises of unreacted mono-, di- and/or trialkyl substituted benzene and hydroxy ketone.

A first fraction comprising ketone is taken at top of the dividing wall distillation column 102' in line 110'. The ketone fraction taken at the top of the dividing wall distillation column 102' may be acetone. The product rate of the first fraction taken at the top of the dividing wall distillation column 102' may be about 30,335 kg/h. The product rate of the acetone in the first fraction taken at the top of the dividing wall distillation column 102' may be about 23,547 kg/h. There may be at least about 95% of ketone present in the cleavage product before the distillation step. The first fraction removed from the dividing wall distillation column 102' comprises more than about 99.9% of acetone recovered in line 110'. There may be relatively small amounts of cumene and water along with the acetone in the first fraction taken at the overhead of the dividing wall distillation column 102'.

A second fraction comprising substituted or unsubstituted phenol is taken at the bottom of the dividing wall distillation column 102' in line 112'. The product rate of the second fraction taken at the bottom of the dividing wall distillation column 102' may be about 43,491 kg/h. The product rate of the phenol in the second fraction taken at the bottom of the dividing wall distillation column 102' may be about 42,555 kg/h. The second fraction removed from the dividing wall distillation column 102' comprises more than about 98% of phenol recovered in line 112'. The heavy hydrocarbons, acetol or hydroxyacetone are removed along with phenol in the second fraction at the bottom of the dividing wall distillation column 102'. The concentration of acetol in the second fraction of the dividing wall distillation column 102' may be about 50 wt-ppm.

A third fraction comprising unreacted mono-, di- and/or trialkyl substituted benzene, water, and hydroxy ketone are taken as side stream of the dividing wall distillation column 102' in line 114'. The side stream taken-off in line 114' may be situated below the feed of cleavage product mixture to the dividing wall distillation column 102'. The liquid rate of the side draw in the third fraction taken as the side stream the dividing wall distillation column 102' may be about 8,738 kg/h. The waste water rate of the side draw in the third fraction taken as the side stream the dividing wall distillation column 102' may be 883 kg/h. The remainder of cumene, water, organic acids and essentially all of the alpha-methyl styrene (AMS) are removed as side stream of the dividing wall distillation column 102' in line 114'. The mixture comprising cumene and alpha-methyl styrene (AMS) in the third fraction may be sent to a phenol recovery unit 120'. The side draw of the dividing wall distillation column 102' may be a two-phase mixture comprising water and organic phase. The side draw in line 114' may be cooled to separate the two-phase mixture before sending the stream to a phenol recovery unit 120'.

This embodiment includes enhanced distillation of acetol to the side draw, higher reflux, higher reboiler duty to maintain residual amount of acetol as low as 50 wt-ppm in the second fraction of the dividing wall distillation column 102' in line 112'. The amount of acetol in the second fraction taken at the bottom of dividing wall column 102' is very low that it eliminates the requirement for a chemical treatment reactor for further removing the impurities from the second fraction comprising phenol. Phenol free of impurities may be recycled to the dividing wall distillation column 102' in line 108'. The phenol recycle rate may be 4,656 kg/h.

Figure 3:
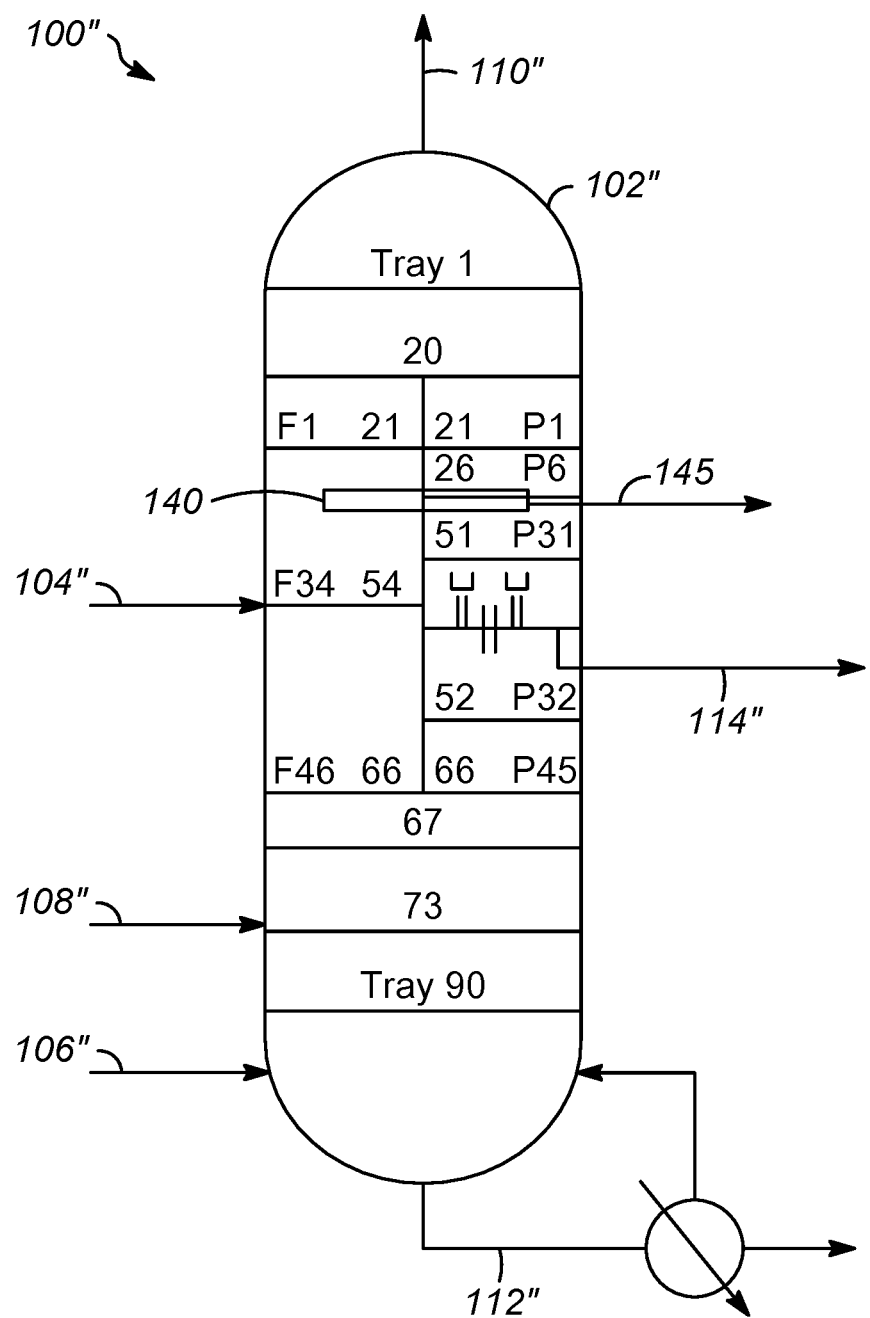
FIG. 3 is another embodiment of the process of the present subject matter.

Turning now to FIG. 3, another embodiment of the process of the present subject matter to separate the cleavage product mixture into at least three fractions in a single dividing wall distillation column. The embodiment of FIG. 3 differs from the embodiment of FIGS. 1 and 2 in that the third fraction of the dividing wall distillation column overflows a liquid collection apparatus and flows into a decanter.

The similar components in FIG. 3 that were described above for FIGS. 1 and 2 will not be described again for FIG. 3. Many of the elements in FIG. 3 have the same configuration as in FIGS. 1 and 2 and bear the same reference number. Elements in FIG. 3 that correspond to elements in FIG. 2 but have a different configuration bear the same reference numeral as in FIG. 2 but are marked with a prime symbol (").

The present subject matter, as shown in FIG. 3, includes distillation column and a reactor system 100" to separate the cleavage product mixture into at least three fractions in a single dividing wall distillation column 102' of the reactor system. Many configurations of the present invention are possible, but specific embodiments are presented herein by way of example. A feed of a cleavage product mixture produced in the cleavage of alkylaryl hydroperoxides is passed to the dividing wall distillation column 102" in line 104". Steam is passed along the feed mixture to the dividing wall distillation column 102" in line 106" for stripping. Steam or water is injected between the bottom of the dividing wall distillation column 102" and an injection point in the bottom-third of the dividing wall distillation column 102".

A first fraction comprising ketone is taken at top of the dividing wall distillation column 102" in line 110". The ketone fraction taken at the top of the dividing wall distillation column 102" may be acetone. There may be at least about 95% of ketone present in the cleavage product before the distillation step. There may be relatively small amounts of cumene and water along with the acetone in the first fraction taken at the overhead of the dividing wall distillation column 102".

A second fraction comprising substituted or unsubstituted phenol is taken at the bottom of the dividing wall distillation column 102" in line 112". The heavy hydrocarbons, acetol or hydroxyacetone are removed along with phenol in the second fraction at the bottom of the dividing wall distillation column 102". The second fraction removed at the bottom of the dividing wall distillation column 102" in line 112" is passed to a chemical treatment reactor (not shown in the FIG. 3). The concentration of acetol in the second fraction of the distillation column may be in the range of about 100 wt-ppm to about 500 wt-ppm. Acetol and other carbonyl impurities are removed from the second fraction of the dividing wall distillation column 102" by treating with amine in the chemical treatment reactor. Phenol free of acetol and other impurities from the chemical treatment reactor may be passed to a crude phenol column. Phenol may be recycled to the dividing wall distillation column 102" in line 108".

A third fraction comprising unreacted mono-, di- and/or trialkyl substituted benzene, water, and hydroxy ketone is taken as side stream of the dividing wall distillation column 102" in line 114". The side stream taken-off in line 114" may be situated below the feed of cleavage product mixture to the dividing wall distillation column 102". The remainder of cumene, water, organic acids and essentially all of the alpha-methyl styrene (AMS) are removed as side stream of the dividing wall distillation column 102" in line 114". The mixture comprising cumene and alpha-methyl styrene (AMS) in the third fraction may be sent to a phenol recovery unit (not shown in FIG. 3). The side draw of the dividing wall distillation column 102" may be a two-phase mixture comprising water and organic phase. The third fraction may overflow a liquid collection apparatus and flow into a decanter 140. The decanter 140 may be located within the dividing wall distillation column 102". The main function of the decanter is to remove the water phase from the column separately from the organic phase, so as to allow the organic phase to be removed from a point further down the column than would be possible without the decanter. The aqueous stream 145 is removed from decanter. The decanter diameter may be about 12.5 feet. The internal decanter settling area may be about 122 square feet and the total decanter area may be about 160 square feet. The internal decanter tangent length may be about 21 feet. The decanter diameter and area would depend on the diameter of the column, which in turn would depend on the capacity of the column and the reflux ratios and/or boil up ratios.

The operating conditions for the dividing wall distillation column 102" will include an operating temperature in the range of from about 174° C. to about 225° C. and a pressure in the range of about 70 kPa to about 345 kPa. The tray spacing of the dividing wall distillation column 102" below the feed of cleavage product mixture is increased from about 680 mm to about 1450 mm. The tray spacing of the dividing wall distillation column 102" above the side stream is increased from about 450 mm to about 2100 mm. There may be about 60 to about 62 theoretical stages in the dividing wall distillation column. The recovery of acetol into the side stream in line 114" is about 50% relative to the feed.

While the subject matter has been described with what are presently considered the preferred embodiments, it is to be understood that the subject matter is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the subject matter is a process for the work-up by distillation of cleavage product mixtures produced in the cleavage of alkylaryl hydroperoxides, which comprises resolving the cleavage product mixture into at least three fractions in a single distillation step by: feeding the cleavage product mixture to a side of a dividing wall distillation column; removing a first fraction comprising ketone at the top of the dividing distillation column comprises at least 95% of a ketone present in the cleavage product before the distillation step; removing a second fraction comprising substituted or unsubstituted phenol at the bottom of the dividing wall distillation column; and removing a third fraction comprising unreacted mono-, di- and/or trialkyl substituted benzene, water and hydroxy ketone as side stream, whereby the side stream take-off is situated below the feed of cleavage product mixture to the dividing wall distillation column. An embodiment of the invention is one, any or all of prior embodiments in this paragraph up through the first embodiment in this paragraph wherein the ketone is acetone. An embodiment of the invention is one, any or all of prior embodiments in this paragraph up through the first embodiment in this paragraph wherein the second fraction is sent to a chemical treatment reactor. An embodiment of the invention is one, any or all of prior embodiments in this paragraph up through the first embodiment in this paragraph wherein the chemical treatment reactor is located within the dividing wall distillation column. An embodiment of the invention is one, any or all of prior embodiments in this paragraph up through the first embodiment in this paragraph wherein the chemical treatment reactor is located outside of the dividing wall distillation column. An embodiment of the invention is one, any or all of prior embodiments in this paragraph up through the first embodiment in this paragraph wherein a steam or water is injected between the bottom of the dividing wall distillation column and an injection point in the bottom-third of the dividing wall distillation column. An embodiment of the invention is one, any or all of prior embodiments in this paragraph up through the first embodiment in this paragraph wherein acetol and other carbonyl impurities are removed from the second fraction of distillation column by treating with amine in the chemical treatment reactor. An embodiment of the invention is one, any or all of prior embodiments in this paragraph up through the first embodiment in this paragraph the pressure of the dividing wall distillation column is about 70 kPa to about 345 kPa and the temperature at the bottom of the dividing wall distillation column is about 174° C. to about 225° C.

A second embodiment of the invention is a process for the work-up by distillation of cleavage product mixtures produced in the cleavage of alkylaryl hydroperoxides, which comprises resolving the cleavage product mixture into at least three fractions in a single distillation step by: feeding the cleavage product mixture to a side of a dividing wall distillation column; removing a first fraction comprising ketone at the top of the dividing wall distillation column comprises at least 95% of a ketone present in the cleavage product before the distillation step; removing a second fraction comprising substituted or unsubstituted phenol at the bottom of the dividing wall distillation column; removing a third fraction comprising unreacted mono-, di- and/or trialkyl substituted benzene, water and hydroxy ketone as side stream of the dividing wall distillation column, whereby the side stream take-off is situated below the feed of cleavage product mixture to the dividing wall distillation column; and sending the second fraction to a chemical treatment reactor. An embodiment of the invention is one, any or all of prior embodiments in this paragraph up through the second embodiment in this paragraph wherein the ketone is acetone. An embodiment of the invention is one, any or all of prior embodiments in this paragraph up through the second embodiment in this paragraph wherein tray spacing of the dividing wall distillation column is increased from about 680 mm to about 1450 mm and tray spacing of the dividing wall distillation column above the side stream is increased from about 450 mm to about 2100 mm. An embodiment of the invention is one, any or all of prior embodiments in this paragraph up through the second embodiment in this paragraph wherein acetol and other carbonyl impurities are removed from the second fraction of distillation column by treating with amine in the chemical treatment reactor. An embodiment of the invention is one, any or all of prior embodiments in this paragraph up through the second embodiment in this paragraph wherein the pressure of the dividing wall distillation column is about 70 kPa to about 345 kPa and the temperature at the bottom of the dividing wall distillation column is about 174° C. to 225° C. An embodiment of the invention is one, any or all of prior embodiments in this paragraph up through the second embodiment in this paragraph wherein the third fraction overflows a liquid collection apparatus and flows into a decanter. An embodiment of the invention is one, any or all of prior embodiments in this paragraph up through the second embodiment in this paragraph wherein the decanter is located within the dividing wall distillation column. An embodiment of the invention is one, any or all of prior embodiments in this paragraph up through the second embodiment in this paragraph wherein the cleavage product mixture before the work-up distillation comprises a concentration of about 40 mol % ketone, about 40 mol % substituted or unsubstituted phenol, and remainder comprises of unreacted mono-, di- and/or trialkyl substituted benzene and hydroxy ketone.

A third embodiment of the invention is a process for the work-up by distillation of cleavage product mixtures produced in the cleavage of alkylaryl hydroperoxides, which comprises resolving the cleavage product mixture into at least three fractions in a single distillation step by: feeding the cleavage product mixture to a side of a dividing wall distillation column; removing a first fraction comprising ketone at the top of the dividing wall distillation column comprises at least 95% of a ketone present in the cleavage product before the distillation step; removing a second fraction comprising substituted or unsubstituted phenol at the bottom of the dividing wall distillation column; sending the second fraction to a chemical treatment reactor; removing a third fraction comprising unreacted mono-, di- and/or trialkyl substituted benzene, water and hydroxy ketone as side stream of the dividing wall distillation column, whereby the side stream take-off is situated below the feed of cleavage product mixture to the distillation column; and the third fraction overflows a liquid collection apparatus and flows into a decanter. An embodiment of the invention is one, any or all of prior embodiments in this paragraph up through the third embodiment in this paragraph wherein a steam or water is injected between the bottom of the dividing wall distillation column and an injection point in the bottom-third of the dividing wall distillation column. An embodiment of the invention is one, any or all of prior embodiments in this paragraph up through the third embodiment in this paragraph wherein the pressure of the distillation column is about 70 kPa to about 345 kPa and the temperature at the bottom of the distillation column is about 174° C. to about 225° C. An embodiment of the invention is one, any or all of prior embodiments in this paragraph up through the third embodiment in this paragraph wherein the recovery of acetol into the side stream is about 50% relative to the feed and the concentration of acetol in the second fraction of the distillation column is about 100 wt-ppm to about 500 wt-ppm.

Without further elaboration, it is believed that using the preceding description that one skilled in the art can utilize the present subject matter to its fullest extent and easily ascertain the essential characteristics of this subject matter, without departing from the spirit and scope thereof, to make various changes and modifications of the subject matter and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:
1. A process for the work-up by distillation of cleavage product mixtures produced in the cleavage of alkylaryl hydroperoxides, which comprises resolving the cleavage product mixture into at least three fractions in a single distillation step by:
  feeding the cleavage product mixture to a side of a dividing wall distillation column;
  removing a first fraction comprising ketone at the top of the dividing wall distillation column comprises at least 95% of a ketone present in the cleavage product before the distillation step;

removing a second fraction comprising of substituted or unsubstituted phenol at the bottom of the dividing wall distillation column; and removing a third fraction comprising unreacted mono-, di- and/or trialkyl substituted benzene, water, and hydroxy ketone as side stream, whereby the side stream take-off is situated below the feed of cleavage product mixture to the dividing wall distillation column.

2. The process of claim 1, wherein the ketone is acetone.

3. The process of claim 1, wherein the second fraction is sent to a chemical treatment reactor.

4. The process of claim 3, wherein the chemical treatment reactor is located within the dividing wall distillation column.

5. The process of claim 3, wherein the chemical treatment reactor is located outside of the dividing wall distillation column.

6. The process of claim 1, wherein a steam or water is injected between the bottom of the dividing wall distillation column and an injection point in the bottom-third of the dividing wall distillation column.

7. The process of claim 3, wherein acetol and other carbonyl impurities are removed from the second fraction of the dividing wall distillation column by treating with amine in the chemical treatment reactor.

8. The process of claim 1, the pressure of the dividing wall distillation column is about 70 kPa to about 345 kPa and the temperature at the bottom of the dividing wall distillation column is about 174° C. to about 225° C.

9. A process for the work-up by distillation of cleavage product mixtures produced in the cleavage of alkylaryl hydroperoxides, which comprises resolving the cleavage product mixture into at least three fractions in a single distillation step by:
   feeding the cleavage product mixture to a side of a dividing wall distillation column;
   removing a first fraction comprising ketone at the top of the dividing wall distillation column comprises at least 95% of a ketone present in the cleavage product before the distillation step;
   removing a second fraction comprising substituted or unsubstituted phenol at the bottom of the dividing wall distillation column;
   removing a third fraction comprising unreacted mono-, di- and/or trialkyl substituted benzene, water and hydroxy ketone as side stream of the distillation column, whereby the side stream take-off is situated below the feed of cleavage product mixture to the dividing wall distillation column; and
   sending the second fraction to a chemical treatment reactor.

10. The process of claim 9, wherein the ketone is acetone.

11. The process of claim 9, wherein tray spacing of the dividing wall distillation column below the feed of cleavage product mixture is increased from about 680 mm to about 1450 mm and tray spacing of the dividing wall distillation column above the side stream is increased from about 450 mm to about 2100 mm.

12. The process of claim 9, wherein acetol and other carbonyl impurities are removed from the second fraction of distillation column by treating with amine in the chemical treatment reactor.

13. The process of claim 9, wherein the pressure of the dividing wall distillation column is about 70 kPa to about 345 kPa and the temperature at the bottom of the dividing wall distillation column is about 174° C. to 225° C.

14. The process of claim 9, wherein the third fraction overflows a liquid collection apparatus and flows into a decanter.

15. The process of claim 14, wherein the decanter is located within the dividing wall distillation column.

16. The process of claim 9, wherein the cleavage product mixture before the work-up distillation comprises a concentration of about 40 mol % ketone, about 40 mol % substituted or unsubstituted phenol, and remainder comprises of unreacted mono-, di- and/or trialkyl substituted benzene and hydroxy ketone.

17. A process for the work-up by distillation of cleavage product mixtures produced in the cleavage of alkylaryl hydroperoxides, which comprises resolving the cleavage product mixture into at least three fractions in a single distillation step by:
   feeding the cleavage product mixture to a side of a dividing wall distillation column;
   removing a first fraction comprising ketone at the top of the dividing wall distillation column comprises at least 95% of a ketone present in the cleavage product before the distillation step;
   removing a second fraction comprising substituted or unsubstituted phenol at the bottom of the dividing wall distillation column;
   sending the second fraction to a chemical treatment reactor;
   removing a third fraction comprising unreacted mono-, di- and/or trialkyl substituted benzene, water and hydroxy ketone as side stream of the dividing wall distillation column, whereby the side stream take-off is situated below the feed of cleavage product mixture to the distillation column; and
   the third fraction overflows a liquid collection apparatus and flows into a decanter.

18. The process of claim 17, wherein a steam or water is injected between the bottom of the dividing wall distillation column and an injection point in the bottom-third of the dividing wall distillation column.

19. The process of claim 17, wherein the pressure of the distillation column is about 70 kPa to about 345 kPa and the temperature at the bottom of the distillation column is about 174° C. to about 225° C.

20. The process of claim 17, wherein the recovery of acetol into the side stream is about 50% relative to the feed and the concentration of acetol in the second fraction of the distillation column is about 100 wt-ppm to about 500 wt-ppm.

* * * * *